United States Patent [19]

Fuchs et al.

[11] Patent Number: 5,441,607
[45] Date of Patent: Aug. 15, 1995

[54] RECOVERY OF CAPROLACTAM FROM DISTILLATION RESIDUES OBTAINED IN THE PURIFICATION OF CAPROLACTAM

[75] Inventors: Hugo Fuchs; Josef Ritz, both of Ludwigshafen; Hans J. Wilfinger, Schifferstadt; David Weatherford, Mannheim, all of Germany

[73] Assignee: BASF Aktiengesellschaft, Ludwigshafen, Germany

[21] Appl. No.: 265,740

[22] Filed: Jun. 27, 1994

[30] Foreign Application Priority Data

Jul. 9, 1993 [DE] Germany .................. 43 22 953.0

[51] Int. Cl.$^6$ .................. B01D 3/34; C07D 201/16
[52] U.S. Cl. .................. 203/49; 203/92; 203/95; 540/540
[58] Field of Search .................. 203/37, 49, 92, 95, 203/100, 47; 540/540

[56] References Cited

U.S. PATENT DOCUMENTS

| | | | |
|---|---|---|---|
| 4,457,807 | 7/1984 | Rulkene et al. | 203/100 |
| 4,582,642 | 4/1986 | Crescentini et al. | 540/540 |
| 4,720,328 | 1/1988 | Corbin et al. | 203/37 |
| 4,764,607 | 8/1988 | Balint et al. | 203/58 |
| 4,767,503 | 8/1988 | Crescentini et al. | 203/48 |
| 4,892,624 | 1/1990 | Fuchs et al. | 203/37 |

FOREIGN PATENT DOCUMENTS

| | | |
|---|---|---|
| 306874 | 7/1990 | European Pat. Off. . |
| 950726 | 10/1956 | Germany . |
| 0215508 | 9/1988 | Japan . |

OTHER PUBLICATIONS

CA: 90: 126973.
CA: 80: 134014.
CA: 104: 191397.
CA: 84: 18020.
*Chem. Abst.* vol. 76, No. 6, Feb. 7, 1972 (English abstract of JP-A 46 024 388).
Derwent Publications Ltd., Week 7743, AN 77-76353Y (English abstract of JP-A 50 123 690).

*Primary Examiner*—Virginia Manoharan
*Attorney, Agent, or Firm*—Keil & Weinkauf

[57] ABSTRACT

Recovery of caprolactam and of an alkali metal carbonate from distillation residues which are obtained in the purification of caprolactam and contain caprolactam and/or oligomers and/or polymers of caprolactam and also alkali metal hydroxides by (a) melting the distillation residues, the caprolactam and/or oligomers and/or polymers of caprolactam and alkali metal hydroxides,
(b) continuously removing caprolactam from the melt,
(c) after removing caprolactam, cooling the melt and obtaining a residue,
(d) dissolving the residue thus obtained in water and
(e) subjecting the aqueous solution thus obtained to combustion with the formation of an alkali metal carbonate is described.

6 Claims, No Drawings

RECOVERY OF CAPROLACTAM FROM DISTILLATION RESIDUES OBTAINED IN THE PURIFICATION OF CAPROLACTAM

The present invention relates to a process for recovering caprolactam and an alkali metal carbonate from distillation residues which are obtained in the purification of caprolactam and contain caprolactam and/or oligomers and/or polymers of caprolactam and also alkali metal hydroxides.

In addition, the invention relates to the use of distillation residues which are obtained in the purification of caprolactam and contain caprolactam and/or oligomers and/or polymers of caprolactam and also alkali metal hydroxides for the recovery of caprolactam and of an alkali metal carbonate.

Caprolactam is in general separated from low-boiling and high-boiling products by distillation during its preparation for the purposes of purification.

The high-boiling distillation residues obtained in this process as a rule still contain caprolactam, its oligomers and polymers and also other impurities and decomposition products. During distillation in the presence of alkali metal-containing compounds, these are customarily also contained in the residues, usually in the form of their hydroxides.

Such distillation residues can contain a relatively high proportion of oligomers of caprolactam if the caprolactam which is obtained from a cracking plant is worked up together with freshly prepared caprolactam.

EP-A 306 874 describes a process for working up distillation residues which are obtained in the purification of caprolactam in which the distillation residues are heated to from 250° to 500° C. in the presence of sodium hydroxide and potassium hydroxide and in the presence of a high-boiling hydrocarbon and caprolactam is continuously removed from the reaction mixture. A disadvantage of this process is that the residue obtained in this case can only be processed with difficulty and in general, to remove it from the reaction vessel, it has to be broken into manageable pieces. In addition, a viscous suspension is customarily obtained in the attempt to dissolve this residue in water. Both the disposal of this suspension by means of a biological treatment plant and disposal by landfill were uneconomical until now. A further disadvantage in the process of EP-A 306 874 is that the high-boiling hydrocarbons used in general have to be purified and in some cases even have to be disposed of by combustion.

It is an object of the present invention to make available a process for recovering caprolactam and an alkali metal carbonate from distillation residues which are obtained in the purification of caprolactam and contain caprolactam and/or oligomers and/or polymers of caprolactam and also alkali metal hydroxides, in which the use of high-boiling hydrocarbons is avoided and the residue obtained is brought into a water-soluble form with recovery of a reutilizable alkali metal carbonate.

We have found that this object is achieved by a process for recovering caprolactam and an alkali metal carbonate from distillation residues which are obtained in the purification of caprolactam and contain caprolactam and/or oligomers and/or polymers of caprolactam and also alkali metal hydroxides, by (a) melting the distillation residues, the caprolactam and/or oligomers and/or polymers of caprolactam and alkali metal hydroxides, (b) continuously removing caprolactam from the melt, (c) after removing caprolactam, cooling the melt and obtaining a residue, (d) dissolving the residue thus obtained in water and (e) subjecting the aqueous solution thus obtained to combustion with the formation of an alkali metal carbonate.

In addition, the use of distillation residues which are obtained in the purification of caprolactam and contain caprolactam and/or oligomers and/or polymers of caprolactam and also alkali metal hydroxides, for recovering caprolactam and an alkali metal carbonate was discovered.

The procedure according to the invention starts from distillation residues which are obtained in the purification of caprolactam and contain caprolactam and/or oligomers and/or polymers of caprolactam and also at least one alkali metal hydroxide. Such distillation residues are obtained, for example, after distillative removal of caprolactam in the presence of an alkali metal hydroxide at bottom temperatures in the range from 120° to 150° C. under reduced pressure, for example at a pressure in the range from 1 to 50 mbar.

A suitable distillation residue according to the invention as a rule has the following composition:
Caprolactam: from 1 to 60, preferably from 10 to 50% by weight
Oligomers and polymers of caprolactam: from 1 to 30, preferably from 5 to 20% by weight
Alkali metal hydroxide: from 1 to 20, preferably from 1 to 10% by weight
Residue (impurities and decomposition products): 100 —sum of the abovementioned constituents.

As a rule, the distillation residue is melted by heating it to temperatures in the range from 120 to 400, preferably from 150° to 350° C., at pressures in the range from 20 to 1013 hPa.

According to the invention, caprolactam is removed continuously from the melt. A preferred embodiment in order to achieve this consists in passing superheated steam or inert gases such as nitrogen, carbon dioxide, rare gases or flue gases through the melt. Superheated steam and nitrogen are particularly suitable. 10–6000 l/h, preferably 1000–3000 l/h, of gas per kg of distillation residue are customarily passed through the melt. When using superheated steam, 0.1–20 parts by weight of steam per kg of melt are particularly used.

In a further preferred embodiment, caprolactam is removed continuously from the melt by applying a reduced pressure, ie. a pressure in the range from 20 to 1013, preferably from 20 to 100 hPa, on its own or by additional use of superheated steam or inert gases.

The caprolactam recovered from the melt is as a rule condensed by cooling or separated by washing with a suitable solvent such as water. If superheated steam and/or inert gases are additionally used, these can expediently be recycled.

The caprolactam obtained according to the invention can be purified, if desired, by customary measures such as distillation and/or crude lactam (ie. not pure caprolactam), which is obtained in the Beckmann rearrangement after neutralization, can be added.

After the removal of the caprolactam, according to the reaction the melt is allowed to cool and the cooled residue is dissolved in water at a temperature which is customarily in the range from 20 to 100, preferably from 30° to 80° C. The weight ratio of residue to water is in general in the range from 0.05:1 to 10:1, preferably from 0.1:1 to 2:1.

The aqueous solution obtained according to the invention is combusted in a combustion plant known per se at temperatures which are in the range from 900 to 1200, preferably from 1000° to 1100° C., obtaining an alkali metal carbonate such as soda or potash or a mixture thereof.

The purity of the alkali metal carbonates such as soda or potash obtained according to the invention is in general at least 99.5%.

The alkali metal carbonate obtained according to the invention is a starting substance which can be used widely, for example for the glass industry and the soap industry. In particular, soda can be used as a replacement for sodium hydroxide.

In addition to the recovery of caprolactam, the advantages of the present invention consist, in comparison with EP-A 306 874 as the nearest prior art, in avoiding the use of high-boiling hydrocarbons and bringing the residue obtained into a water-soluble form with recovery of a reutilizable alkali metal carbonate.

EXAMPLES

EXAMPLE 1

195 g of a distillation residue from caprolactam purification, containing 46.3% by weight of caprolactam, 5% by weight of sodium hydroxide and also oligomers, impurities and decomposition products, were heated to 315° C. and thus melted. 600 g of steam at 350° C. were then passed through the melt in the course of 5 h obtaining 62 g of a water-soluble residue. The residue was taken up in 150 ml of water at room temperature and then combusted by spraying into a flame at 1000° C. 12.5 g of soda were obtained as a combustion residue. The steam/caprolactam mixture escaping from the reaction vessel was condensed obtaining 133 g of caprolactam.

EXAMPLE 2

521 g of a distillation residue from caprolactam purification, containing 46.3% by weight of caprolactam, 5.3% by weight of sodium hydroxide and also oligomers, impurities and decomposition products, were heated to 340° C. and thus melted. 240 ml of steam at 340°C. were then passed through the melt (flow rate: 0.12 l/h) obtaining a water-soluble residue. The residue was taken up in 350 ml of water at 50°C. and then combusted by spraying into a flame at 1000°C. 35 g of soda were obtained as a combustion residue. The steam/caprolactam mixture escaping from the reaction vessel was condensed obtaining 396 g of caprolactam.

We claim:

1. A process for recovering caprolactam and an alkali metal carbonate from distillation residues which are obtained in the purification of caprolactam and contain caprolactam and oligomers of caprolactam and also alkali metal hydroxides, which comprises
    (a) melting the distillation residues, the caprolactam and obligomers of caprolactam and alkali metal hydroxides,
    (b) continuously removing caprolactam from the melt,
    (c) cooling the melt to obtain a residue,
    (d) dissolving the residue in water and
    (e) subjecting the aqueous solution thus obtained to combustion with the formation of an alkali metal carbonate.

2. The process of claim 1, wherein caprolactam is removed from the melt using superheated steam or an inert gas.

3. The process of claim 1, wherein superheated steam or an inert gas having a temperature in the range of from 250° to 450° C. is used to remove the caprolactam from the melt.

4. The process of claim 1, wherein the alkali metal hydroxide is sodium hydroxide or potassium hydroxide or a mixture thereof.

5. The process of claim 1, wherein the caprolactam is removed from the melt by applying a reduced pressure.

6. The process of claim 1, wherein the distillation residues obtained in the purification of caprolactam also contain polymers of caprolactam.

* * * * *

UNITED STATES PATENT AND TRADEMARK OFFICE
CERTIFICATE OF CORRECTION

PATENT NO. : 5,441,607
DATED : August 15, 1995
INVENTOR(S) : FUCHS et al.

It is certified that error appears in the above-indentified patent and that said Letters Patent is hereby corrected as shown below:

Column 4, claim 1, line 18, "and obligomers" should read --and oligomers--.

Signed and Sealed this

Thirty-first Day of October 1995

Attest:

BRUCE LEHMAN

Attesting Officer

Commissioner of Patents and Trademarks